United States Patent
Aptaker et al.

(10) Patent No.: US 7,041,914 B2
(45) Date of Patent: May 9, 2006

(54) METHOD FOR COMPENSATION OF NEAR-NEIGHBOR SAMPLE EFFECTS IN A NMR CHECK WEIGHING SYSTEM

(75) Inventors: Peter Aptaker, Wantage (GB); James M. McKendry, Headington (GB); Jozef A. W. M. Corver, Nuenen (NL)

(73) Assignee: The BOC Group, Inc., Murray Hill, NJ (US)

( * ) Notice: Subject to any disclaimer, the term of this patent is extended or adjusted under 35 U.S.C. 154(b) by 0 days.

(21) Appl. No.: 10/881,647

(22) Filed: Jun. 30, 2004

(65) Prior Publication Data

US 2005/0247493 A1    Nov. 10, 2005

Related U.S. Application Data

(60) Provisional application No. 60/567,929, filed on May 4, 2004.

(51) Int. Cl.
*G01V 3/00* (2006.01)
*G01G 23/01* (2006.01)
*G01G 19/00* (2006.01)

(52) U.S. Cl. .......... 177/1; 177/25.13; 177/210 R; 177/245; 324/307; 702/101; 73/1.13

(58) Field of Classification Search .......... 177/1, 177/25.11–25.19, 50, 185, 210 R, 245; 324/300, 324/307–315; 702/101; 73/1.13
See application file for complete search history.

(56) References Cited

U.S. PATENT DOCUMENTS

| | | | | |
|---|---|---|---|---|
| 3,796,873 A | | 3/1974 | Ledgett .......... 177/1 |
| 4,529,050 A | * | 7/1985 | Mosher et al. .......... 177/1 |
| 4,556,847 A | * | 12/1985 | Aspiotis et al. .......... 324/307 |
| 4,709,770 A | * | 12/1987 | Kohashi et al. .......... 177/50 |
| 4,727,325 A | | 2/1988 | Matsui et al. .......... 324/309 |
| 5,015,954 A | | 5/1991 | Dechene et al. .......... 324/307 |
| 5,049,819 A | | 9/1991 | Dechene et al. .......... 324/307 |
| 5,291,422 A | | 3/1994 | Esztergar .......... 702/30 |
| 5,302,894 A | | 4/1994 | Hrubes .......... 324/207.16 |
| 5,780,777 A | * | 7/1998 | Selig .......... 177/25.11 |

(Continued)

FOREIGN PATENT DOCUMENTS

DE    1803372 A1    5/1970

(Continued)

OTHER PUBLICATIONS

Derwent WPI Abstract, UNILEVER NV, Package Weight Measuring System, NL 154001B, Jul. 15, 1977 (Corresponds to DE 1803372A1).

*Primary Examiner*—Randy W. Gibson
(74) *Attorney, Agent, or Firm*—Ira L. Zebrak; Bernard Lau (57) ABSTRACT

A method (10) for reducing or eliminating the effects of proximate samples on the NMR measurement of the mass of a test sample in a NMR check weighing system (24) for samples on a production line. The test sample is in a container (22) on a production line with the plurality of proximate samples each also in a container (22) on the production line. Method (10) includes determining cross coupling weighing factors for a plurality of samples in proximity to the test sample, magnetic resonance measuring of the test sample and proximate samples, the step of magnetic resonance measuring of the test sample and proximate samples providing data representative of each measurement; and applying weighing factors to the data representative of each measurement compensating for the proximate sample effects.

14 Claims, 4 Drawing Sheets

U.S. PATENT DOCUMENTS

| | | | |
|---|---|---|---|
| 6,028,428 A | 2/2000 | Cunningham et al. | 324/314 |
| 6,362,619 B1 | 3/2002 | Prammer et al. | 324/303 |
| 6,377,049 B1 | 4/2002 | Benz et al. | 324/319 |
| 6,426,058 B1 | 7/2002 | Pines et al. | 424/9.3 |
| 6,759,601 B1 * | 7/2004 | Petty et al. | 177/1 |
| 6,946,838 B1 * | 9/2005 | Corver et al. | 324/307 |
| 2004/0231699 A1 | 11/2004 | Corver | 134/3 |
| 2004/0251904 A1 | 12/2004 | Corver et al. | 324/321 |

FOREIGN PATENT DOCUMENTS

| | | |
|---|---|---|
| GB | 2149509 A | 6/1985 |
| WO | WO 99/67606 A1 | 12/1999 |

* cited by examiner

METHOD FOR COMPENSATION OF NEAR-NEIGHBOR SAMPLE EFFECTS IN A NMR CHECK WEIGHING SYSTEM

CROSS REFERENCE TO RELATED APPLICATION

This application claims the benefit of the filing date of U.S. Provisional Application Ser. No. 60/567,929, filed May 4, 2004, which is incorporated herein by reference.

FIELD OF THE INVENTION

The present invention relates to check weighing material in a container, while the container is moving in a production line, using nuclear magnetic resonance (NMR) techniques. More particularly, the present invention relates to a method for compensation of the effects of near neighbor containers and their samples at the time of a NMR check weighing measurement.

BACKGROUND

The use of NMR techniques in measurement, detection and imaging has become desirable in many scientific fields of endeavor. The non-invasive, non-destructive nature of NMR has facilitated application to industrial instrumentation, analysis and control tasks, in a variety of applications, including but not limited to cosmetics, perfumes, industrial chemicals, biological samples and food products. As one example, check weighing is used by the pharmaceuticals industry for monitoring and regulating the amount of drug in a sealed glass vial during filling. The drug weight can be as small as a fraction of a gram, and is required to be weighed with an accuracy of a few percent or better, in a vial weighing tens of grams at a rate of several weighings per second.

International Patent Application No. WO 99/67606, incorporated herein by reference as if fully written out below, describes a check weighing system for samples on a production line using NMR techniques. This system includes a magnet for creating a static magnetic field over an interrogation zone to produce a net magnetisation within a sample located within the interrogation zone, and a RF coil for applying an alternating magnetic field over the interrogation zone to cause excitation of the sample according to the principles of NMR.

As is well known in the NMR art, after pulse excitation of the sample by the alternating magnetic field, the sample emits a signal induced in the RF coil, called the free induction decay (FID), from which much information, like sample mass (or weight) can be learned. The FID is directly proportional to the net magnetisation applied to the sample. However, if more than one sample is located on the product filling line within the interrogation zone, and particularly within the alternating magnetic field when a sample is being excited, the additional sample or samples will also develop their own net magnetisation, and emit their own FIDs induced in the RF coil. Consequently, the FID induced in the RF coil in this circumstance is an aggregate of FIDs in which the neighboring samples produce an interference or cross coupling effect. An accurate determination of the mass (or weight) of the single test sample requires that cross coupling effects be minimized or eliminated.

Of course, spacing samples on the production line so that only one sample is located within the interrogation zone at a time would eliminate the potential for cross coupling. This is undesirable from a manufacturing standpoint because it would reduce the rate at which samples may be processed.

It is desirable to provide a method for reducing or eliminating the effects of near neighbor samples on the NMR measurement of the mass of a sample in a NMR check weighing system for samples on a production line.

SUMMARY

There is provided a method for compensation of proximate sample effects in a magnetic resonance check weighing system having a test sample in a container on a production line and a plurality of proximate samples each in a container on the production line, comprising the steps of:

determining cross coupling weighing factors for a plurality of samples in proximity to the test sample;

magnetic resonance measuring of the test sample and proximate samples, said step of magnetic resonance measuring of the test sample and proximate samples providing data representative of each measurement; and applying weighing factors to the data representative of each measurement, compensating for the proximate sample effects.

DETAILED DESCRIPTION

Figure 2:
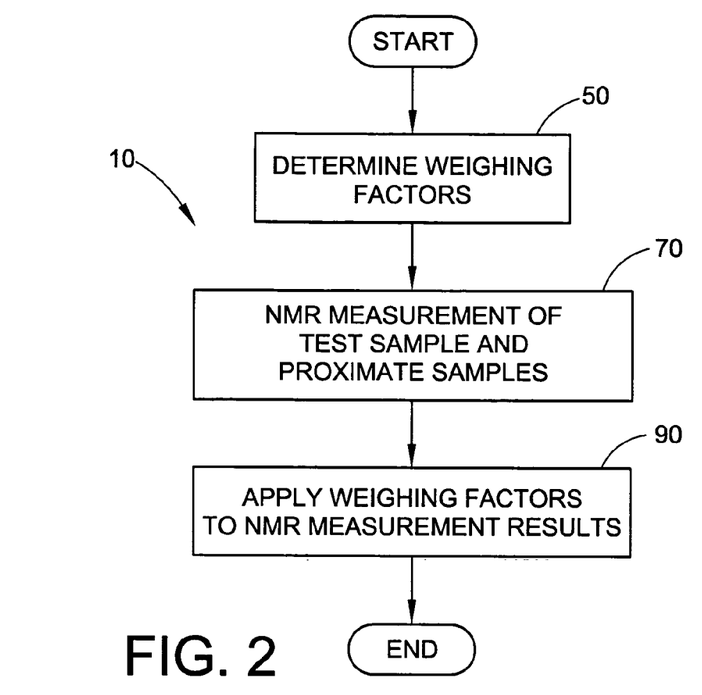
FIG. 2 is a top level flow chart of an exemplary method in accordance with the teachings of the present invention for compensation of proximate sample effects in a NMR check weighing system during production.

A method in accordance with the present invention is indicated generally by the numeral 10 in FIG. 2. This method is used in a non-contact, NMR check weighing system 20 that checks the mass (or weight) of the content of a container while continuously moving in a production line (also known as a "product filling line"). This method compensates for interference from samples in NMR check weighing system 20 that are proximate to a NMR test sample. One exemplary application requiring such check weighing is the packaging of pharmaceuticals. In order to understand best this method, it is helpful to first review certain of the structure of an exemplary NMR check weighing system and its associated production line.

Exemplary NMR Check Weighing System for Pharmaceutical Packaging

Figure 1:
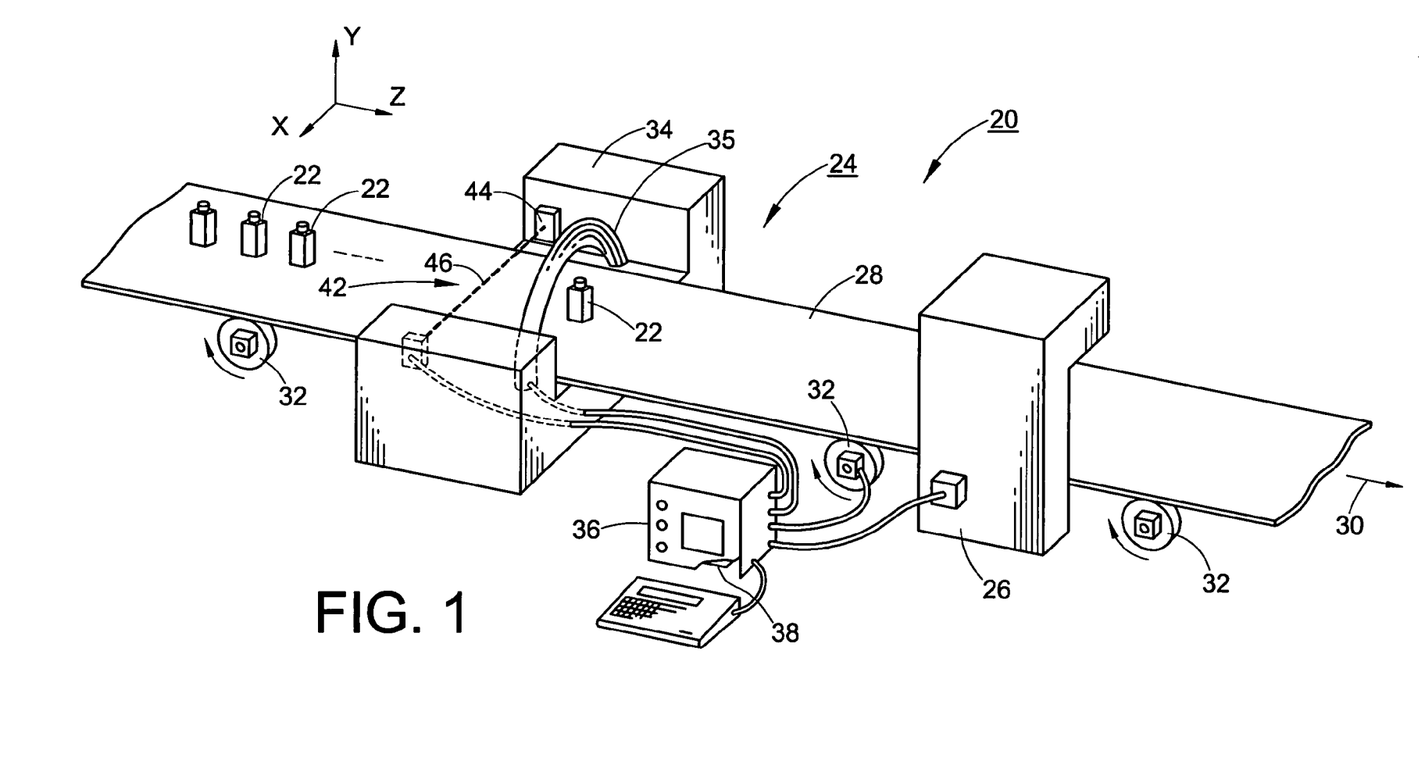
FIG. 1 is a perspective view of a portion of a production line with an exemplary NMR check weighing station for checking that each container passing through the weighing station has the desired amount of product.

FIG. 1 shows a portion of a production line, which fills glass vials 22 with a drug sample. The exemplary check weighing station 24 is provided "in-line" for non-contact weighing of each of the filled vials that pass therethrough, and a reject station 26 that removes those vials from the line that do not have the sufficient amount of the drug to meet product specifications. Vials 22 are transported to check weighing station 24 from a filling (and optionally sealing) station (not shown) by a conveyor having a conveyor belt 28 which, as represented by the arrow 30, moves in the z direction through the action of rotating conveyor wheels 32.

Check weighing station 24 uses NMR techniques to determine the mass of the drug sample within each of the vials 22. As those ordinarily skilled in the art will appreciate, glass vials are useful as the container, because they do not give a signal that might interfere with the measurement process. In this embodiment, check weighing station 24 includes a source of a static magnetic field such as an electromagnet or a permanent magnet 34, RF probe 35, and a computer control system 36 having a processor 38. Magnet 34 creates a homogeneous direct current (DC) or static magnetic field in the x direction across conveyor belt 28 in a region that may be referred to as the interrogation zone 40. Interrogation zone 40 extends the length of conveyor belt 28 through which the static magnetic field is uniformly applied by permanent magnet 34. The sample in vial 22 contains nuclei which each possess a magnetic moment, e.g. 1H nuclei (protons), as a result of the spin of the nuclei. Because the sample protons posses a magnetic moment, the sample is capable of acquiring a net magnetisation when under the influence of certain magnetic fields. When the sample is within interrogation zone 40, the applied static magnetic field creates a net magnetisation within the sample. A vial position detection device 42 preceding or at the start of interrogation zone 40 (such as the optical position sensor 44 having a light beam 46) accurately and precisely detects when vial 22 reaches a known physical position on conveyor belt 28 preceding check weighing station 24.

In most NMR systems, the static magnetic field strength is such that the Larmor frequency of the sample is in the radio frequency range of the electromagnetic spectrum. Applying an alternating current (AC) magnetic field to the sample at the sample's Larmor frequency and orientated orthogonal to the static magnetic field, will cause the sample's net magnetisation to rotate about the AC magnetic field's axis, away from the direction of the static field. In this embodiment, this magnetic field is generated by applying a corresponding AC current to the RF probe 35. Varying the amount of energy delivered to the RF probe 35 can vary the angle of rotation of the net magnetisation.

In this exemplified embodiment, an excitation field that causes a 90° rotation is used to excite the sample. After the 90° pulse has been applied to the sample, the sample is left in a high-energy, non-equilibrium state, from which it will relax back to its original state of equilibrium. As it relaxes, electromagnetic energy at the Larmor frequency is emitted, the magnetic component of which induces a sample reply signal known as the Free Induction Delay (FID) in the form of current in the RF probe 35.

RF probe 35 monitors energy emitted by the sample as the net magnetisation of the sample returns to its original state and generates an output signal having a characteristic which is proportional to the energy emitted. In the present example a characteristic of the induced current, i.e., amplitude, varies with, among other things, the number of magnetic moments in the sample and hence the number of molecules in the sample. The received signal is then passed to the computer control system 36, which compares the amplitude of the signal received from the unknown sample, with the amplitude of a signal received from a calibration sample with a known mass (or weight), to determine the mass (or weight) of the sample being tested.

For illustrative purposes, but not by way of limitation, the general operation of the NMR check weighing system 24 as shown in FIG. 1 will be described. First, check weighing system 24 is initialized, including installing a RF probe 35 appropriate for the sample to be tested. Once production is begun, conveyor belt 28 continuously transports vials 22 whose sample mass (or weight) is to be determined. As each vial 22 reaches a position detected by optical position sensor 44, optical position sensor 44 generates a signal accurately establishing the position of that vial 22 to computer control system 36. Computer control system 36 then tracks the motion of conveyor belt 28 as vial 22 advances to the position $P_M$ within interrogation zone 40 where the sample in vial 22 is measured by magnetic resonance.

At the instant in time when vial 22 is in position $P_M$, a brief energization of RF probe 35 is triggered, applying an alternating magnetic field in interrogation zone 40 such that the net magnetisation of the sample in vial 22 is temporarily changed. RF probe 35 monitors the energy emitted by the sample in vial 22 as the net magnetisation of the sample returns to its original state of equilibrium, and generates an output signal having a characteristic which is proportional to the energy emitted, such as current amplitude. Computer control system 36 receives the RF probe 35 output signal. Processor 38 compares the current amplitude or other output signal characteristic with like data obtained from at least one similar sample of known mass, and determines the mass of the sample from the results of the comparison.

Compensation of Proximate Sample Effects

Processor 38 performs a real time calculation of the masses of the samples in vials 22. Generally the samples are substantially equally spaced on conveyor belt 28 and sufficiently close such that the signal received by RF coil 35 results not just from the sample whose mass is being investigated (the test sample), but also from other samples in vials 22 that also develop a net magnetisation (the proximate or near neighbor samples). This interference effect is referred to as cross coupling and must be eliminated or compensated to obtain an accurate measurement of sample mass. Cross coupling may not be symmetrical about the testing position because samples may have different net magnetisations (due to different times and locations in the permanent magnetic field and/or NMR alternating magnetic field, i.e., different magnetic histories).

Method 10 also compensates for two other effects. First, a position on the conveyor line may be empty, i.e., without a sample or vial 22. In order to compensate for such events, as will be explained below, method 10 processes the signal from all samples, irrespective of mass, including empty spaces with (zero mass). Second, part of the NMR data signal received comes from noise and part comes from sources other than the sample, e.g., from the rubber top of a vial 22 or from conveyor belt 28 carrying the vials 22. Method 10 will include an offset factor, which may be identified as $w_{off}$, to accommodate for internal and external noise.

Method 10 contemplates determination of what may be called weighing factors to compensate for the cross coupling of samples proximate to the test sample, and the other noted effects. The number of samples on either side of the test sample for which compensation must be provided depends on several issues, including how quickly the cross coupling signal decreases from the test position and the accuracy required by the application. We have found that when using a 2 ml volume drug vial 22 filled with a drug in its liquid phase at room temperature, compensating for samples and vials 22 two positions either side of the test sample and vial 22 presently provides an acceptable level of compensation in the pharmaceutical manufacturing industry. In this situation the relationship between the data signal obtained and the true masses of the samples in a set can be expressed as follows:

$$d_i * Sc = W_{off} + W_{-2} * m_{i-2} + W_{-1} * m_{i-1} + W_0 * m_i + w_1 * m_{i+1} + w_2 * m_{i+2} \qquad 1$$

where $m_i$ is the mass of the test sample, $m_{i-1}$ is the mass of one sample position following the test sample, $m_{i+2}$ is the mass of two sample positions following the test sample, $m_{i-1}$ is the mass of one sample position preceding the test sample, $m_{i-2}$ is the mass of two sample positions preceding the test sample, $d_i$ is the NMR measured signal data from the test sample, sc is a scale factor to convert data signal to test sample mass (if not needed, set to 1), $W_0$ is the weighing factor for the test sample, and the remaining terms with w are weighing factors for the position indicated by the subscripts, and $w_{off}$ is the offset factor noted above to accommodate for internal and external noise.

If sufficient accuracy is obtained with only one sample cross coupling either side of the test sample then this relationship simplifies to $$d_i * sc = w_{off} + w_{-1} * m_{i-1} + w_0 * m_i + w_1 * m_{i+1} \qquad 2$$

During the calibration phase $d_i$ and $m_i$ are known and $w_i$ are unknown, whereas during production $d_i$ and $w_i$ are known and $m_i$ are unknown. Method 10 provides an deconvolution process performed iteratively to determine the values of the unknowns.

Turning to FIG. 2, a top level flow chart is shown depicting an exemplary method in accordance with the teachings of the present invention for compensation of proximate sample effects in a NMR check weighing system 24 during production. Method 10 includes steps that must be performed prior to production operation of NMR check weighing system 24 in what may be also called the pre-production or calibration phase, and steps that are performed during production operation. In the pre-production step 50, weighing factors to provide the compensation contemplated by the present invention are determined. Steps 70 and 90 present the respective production steps of NMR measurement of the test sample and the proximate samples, and applying the weighing factors to the data representative of the signals received by RF coil 35, whereby the mass for test sample may be compensated for the cross coupling and the other deleterious effects noted herein.

Figure 3:
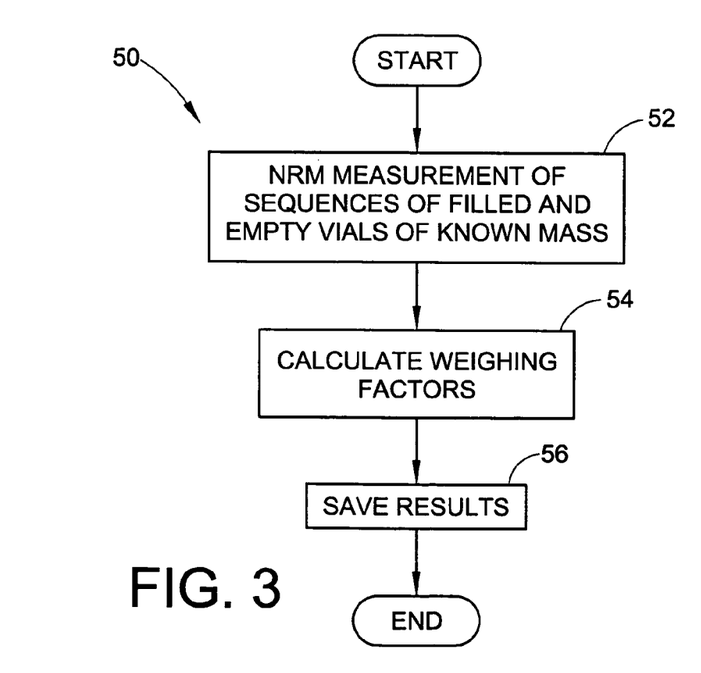
FIG. 3 is a top level flow chart of the pre-production steps in determining weighing factors for compensation of proximate sample effects in a NMR check weighing system, shown as a top level step in FIG. 2.

FIG. 3 is a top level flow chart of the pre-production steps in determining weighing factors for compensation of proximate sample effects in a NMR check weighing system, shown as step 50 in FIG. 2. Step 50 includes making an NMR measurement of sequences of sample filled vials 22 all of known mass and open spaces in step 52, calculating the weighing factors in step 54, and, in step 56, saving the calculated weighing factors 54 such as in computer control system 36.

This is an iterative procedure. An initial estimate of $m_i$ is found in the first cycle of the iteration by ignoring cross coupling i.e. $m_i = (d_i * sc - woff) / w_0$ from equation 1 above. This is C in the table below. In addition the values of the 1st iteration estimated masses of a number of samples either side of i are also set to be equal to $m_i$. These are A, B, D and E in the illustration. The number of samples is determined by the number of iterations required, as explained below. In subsequent iterations the estimated masses are corrected by subtracting the cross coupling from adjacent estimated masses in the previous iteration.

For example $F = B - (w_{-1} * A) - (w_1 * C)$

This procedure converges after a few iterations.

Because of the cross coupling effect, finding the best estimate of the mass of sample I can be only done when the data signals from some subsequent samples have also been received because they will contribute to the NMR signal for sample i and the amount of the contributions will depend on their masses. The illustration below is for the case in which sample I cross couples with only the sample on either of its sides. However, in this case the signal data from sample i+2 is needed before the mass of sample i can be determined, and a minimum of three iterations is required by the deconvolution algorithm. This will ensure that the calculation of the mass of sample i is based only on estimated masses that allow for cross coupling, and to ensure that these estimated masses themselves also have been based on estimated masses that have allowed for cross coupling.

| | | Estimated Mass | | |
|---|---|---|---|---|
| Index | Data | 1st Iteration | 2nd Iteration | 3rd Iteration |
| i − 2 | $d_{i-2}$ | A | | |
| i − 1 | $d_{i-1}$ | B | F | |
| i | $d_i$ | C | G | I |
| i + 1 | $d_{i+1}$ | D | H | |
| i + 2 | $d_{i+2}$ | E | | |

In the above table: I is calculated from F, G and H; F is calculated from A, B and C; G is calculated from B, C and D; and, H is calculated from C, D and E If the number of samples which cross couple is greater than one either side of sample i, then the number of iterations required increases and the number of values of data d also increases. This means that the number of samples beyond i which must have been measured before the mass of i can be determined also increases.

It will be appreciated that the size of the data array depends on the number of samples on either side of sample i whose cross coupling must be taken into account. If two samples either side of sample i are required to determine cross coupling, then the data array will contain eleven values from the center sample whose mass is being calculated. In this instance, the variable "offset" will be set to a value of six to select the center mass to be returned by the function.

Figure 4:
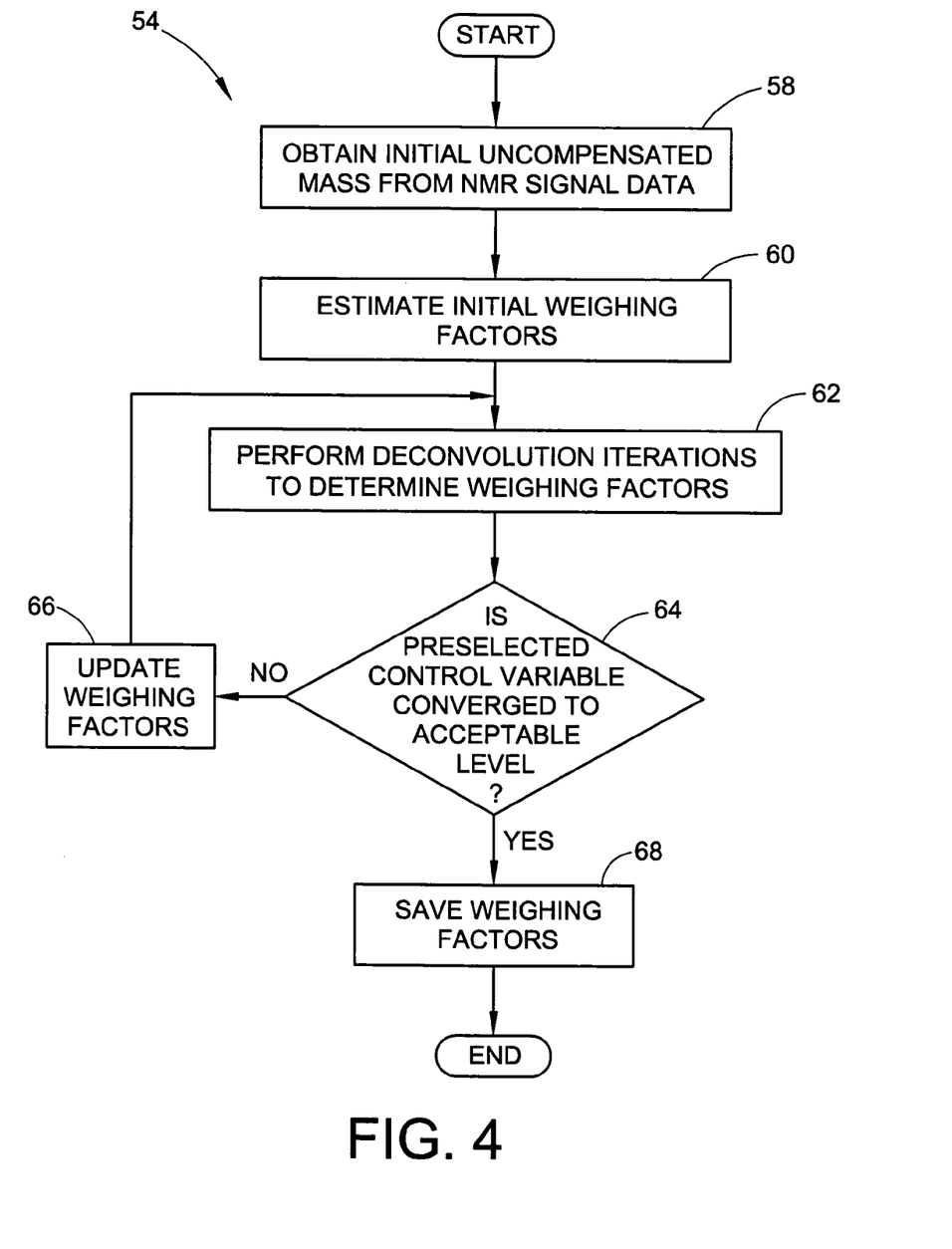
FIG. 4 is an intermediate level flow chart of the pre-production steps in calculating weighing factors during calibration, shown as a top level step in FIG. 3.

FIG. 4 is an intermediate level flow chart of the pre-production steps in calculating weighing factors during calibration, shown as a top level step in FIG. 3. In step 58 the initial uncompensated mass of the samples may be obtained from the NMR signal data. Next, in step 60 a set of initial weighing factors may be estimated for use to initiate the following step 62 in which deconvolution iterations are performed to determine weighing factors. In step 64 a decision is made whether a preselected control variable converged to an acceptable level. If so, the weighing factors are saved in step 68, and this pre-calibration process ended. If not, the weighing factors are updated to those just obtained, as shown in step 66, and the deconvolution process of step 62 and test of step 64, repeated.

One of ordinary skill should now appreciate that when the set of initial weighing factor values is chosen based on previous experience, the values do not need to be exact. The difference between the estimated masses and the true known masses will be minimized with each iteration of the deconvolution algorithm. The procedure stops when the difference in determined mass from one iteration to the next falls below a preselected value, i.e., converges.

It should also now be evident that because the calculation of the mass of sample i requires data from samples which are in front of and also behind it, the mass of sample i can only be calculated after data from a later sample has been received. For example, to determine cross coupling from two samples either side of sample i, a data signal first must be received from sample i+5.

Figure 5:
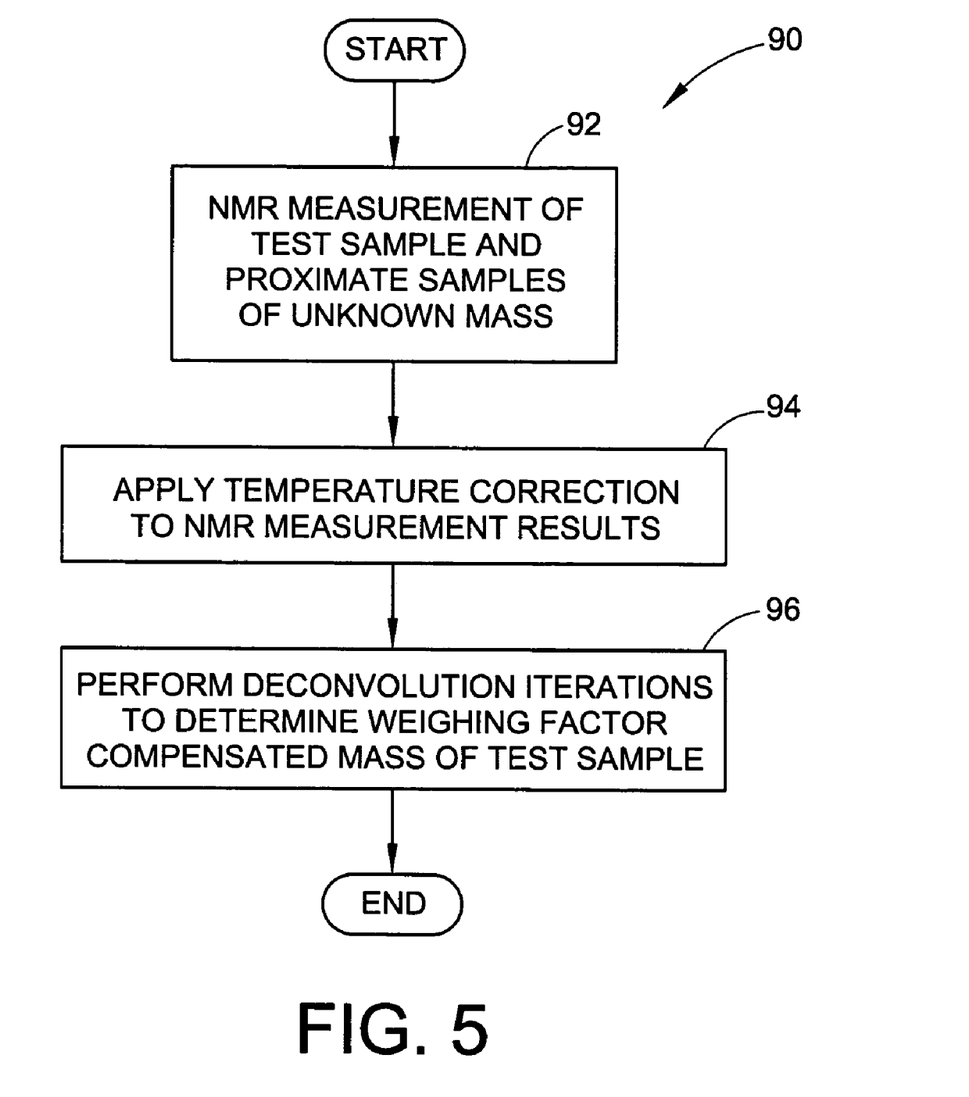
FIG. 5 is an intermediate level flow chart of the steps in applying the weighing factors during production, shown as a top level step in FIG. 2.

FIG. 5 is an intermediate level flow chart of the steps in applying the weighing factors during production, shown as a top level step in FIG. 2. During operation NMR measurements are made of the test sample and the proximate samples, all of unknown mass, as shown in step 92. Next in step 94, and optionally, a temperature correction may be applied to the NMR measurement signal. Finally, in step 96 the same deconvolution iterations used in the calibration phase are performed to determine the weighing factor compensated mass of the test sample. During operation the weighing factors used are those found during the calibration phase. The same iteration process is used to calculate the masses.

The ordinarily skilled artisan should now recognize that a method in accordance with the present invention uses calibration and filtering to extract the relevant data out of an aggregated signal by determining the effect of the two neighbors on both sides of the vial that needs to be measured, and by performing recursively a deconvolution.

It will be understood that the embodiments described herein are merely exemplary and that a person skilled in the art may make many variations and modifications without departing from spirit and scope of the invention. The various embodiments may be practiced in the alternative, or in combination, as appropriate. All such modifications and variations are intended to be included within the scope of the invention as defined in the appended claims.

We claim:

1. A method for compensation of effects of proximate samples in a magnetic resonance check weighing system having a test sample in a container on a production line and a plurality of proximate samples each in a container on the production line, comprising the steps of:
   determining weighing factors comprising cross coupling weighing factors for a plurality of samples in proximity to a calibration test sample;
   magnetic resonance measuring of the test sample and the proximate samples, said step of magnetic resonance measuring of the test sample and the proximate samples providing data representative of each measurement; and
   applying the weighing factors to the data representative of each measurement compensating for the effects of the proximate samples.

2. A method according to claim 1, wherein the step of determining cross coupling weighing factors includes the step of performing magnetic resonance measurement of a sequence of filled container of known mass.

3. A method according to claim 2, wherein the step of determining cross coupling weighing factors further includes the step of performing magnetic resonance measurement of a sequence of filled containers and empty containers of known mass.

4. A method according to claim 2, wherein the step of determining cross coupling weighing factors further includes the step of calculating the weighing factors.

5. A method according to claim 4, wherein the step of calculating the weighing factors in accordance with one of the following relationship and a multiple of the following relationship: $d_i*sc = w_{off} + w_{-1}*m_{i-1} + w_0*m_i + w_1*m_{i+1}$, where $m_i$ is the mass of the calibration test sample, $m_{i+1}$ is the mass of one sample position following the calibration test sample, $m_{i-1}$ is the mass of one sample position preceding the calibration test sample, $d_i$ is the magnetic resonance measured data representative of the calibration test sample, sc is a scale factor to convert data signal to calibration test sample mass, $w_0$ is the weighing factor for the calibration test sample, and the remaining terms with w are weighing factors for the position indicated by the subscripts, and $w_{off}$ is the offset factor to accommodate for internal and external noise.

6. A method according to claim 4, wherein the step of determining cross coupling weighing factors further includes the step of saving the calculated weighing factors.

7. A method according to claim 5, wherein the step of determining cross coupling weighing factors further includes the step of performing a plurality of deconvolution iterations of the said relationship.

8. A method according to claim 7, wherein the step of determining cross coupling weighing factors further includes the step of obtaining an initial uncompensated mass for the calibration test sample from the magnetic resonance measured data representative of the calibration test sample.

9. A method according to claim 8, wherein the step of determining cross coupling weighing factors further includes the step of estimating initial weighing factors.

10. A method according to claim 9, wherein the step of determining cross coupling weighing factors further includes the step of determining whether to repeat the step of deconvolution iteration, including the step of comparing a preselected control variable to a preselected level.

11. A method according to claim 10, wherein the step of determining cross coupling weighing factors further includes the step of one of updating the weighing factors and saving the weighing factors.

12. A method according to claim 1, wherein the step of applying weighing factors the data representative of each measurement includes the step of performing a plurality of magnetic resonance measurements of the test sample and proximate samples of unknown mass.

13. A method according to claim 12, wherein the step of applying weighing factors to the data representative of each measurement further includes the step of applying temperature correction to magnetic resonance measurement.

14. A method according to claim 13, wherein the step of applying weighing factors to the data representative of each measurement further includes the step of performing a plurality of deconvolution iterations to determine weighing factor compensated mass of the test sample.

* * * * *

UNITED STATES PATENT AND TRADEMARK OFFICE
CERTIFICATE OF CORRECTION

PATENT NO. : 7,041,914 B2
APPLICATION NO. : 10/881647
DATED : May 9, 2006
INVENTOR(S) : Aptaker et al.

It is certified that error appears in the above-identified patent and that said Letters Patent is hereby corrected as shown below:

Column 5, Line 21 of the Specification replace " $W_0$ " with -- $w_0$ --.

Column 8, Line 12 of claim 5 replace " $m_{1+1}$ " with -- $m_{i+1}$ --.

Signed and Sealed this

First Day of May, 2007

JON W. DUDAS
*Director of the United States Patent and Trademark Office*